United States Patent
Goldstein et al.

(10) Patent No.: US 11,483,641 B2
(45) Date of Patent: *Oct. 25, 2022

(54) METHODS AND DEVICES FOR RADIO FREQUENCY (RF) MITIGATION PROXIMATE THE EAR

(71) Applicant: Staton Techiya LLC, Delray Beach, FL (US)

(72) Inventors: Steven Wayne Goldstein, Delray Beach, FL (US); Gideon Duvall, Boca Raton, FL (US)

(73) Assignee: Staton Techiya, LLC, Delray Beach, FL (US)

( * ) Notice: Subject to any disclaimer, the term of this patent is extended or adjusted under 35 U.S.C. 154(b) by 361 days.

This patent is subject to a terminal disclaimer.

(21) Appl. No.: 16/666,308

(22) Filed: Oct. 28, 2019

(65) Prior Publication Data
US 2020/0059714 A1 Feb. 20, 2020

Related U.S. Application Data

(63) Continuation of application No. 13/735,175, filed on Jan. 7, 2013, now Pat. No. 10,575,081, which is a
(Continued)

(51) Int. Cl.
*H04R 1/10* (2006.01)
*H04R 31/00* (2006.01)
(Continued)

(52) U.S. Cl.
CPC .......... *H04R 1/1016* (2013.01); *A61F 2/18* (2013.01); *H04R 1/1058* (2013.01);
(Continued)

(58) Field of Classification Search
CPC ...... H04R 1/1016; H04R 1/10; H04R 1/1058; H04R 1/1091; H04R 1/086; H05K 9/00; H05K 9/009; A61F 2/18
See application file for complete search history.

(56) References Cited

U.S. PATENT DOCUMENTS 3,876,843 A 4/1975 Moen
4,054,749 A 10/1977 Suzuki et al.
(Continued)

FOREIGN PATENT DOCUMENTS

EP 1519625 A2 3/2005
WO 2006037156 A1 4/2006

OTHER PUBLICATIONS

Olwal, A. and Feiner S. Interaction Techniques Using Prosodic Features of Speech and Audio Localization. Proceedings of IUI 2005 (International Conference on Intelligent User Interfaces), San Diego, CA, Jan. 9-12, 2005, p. 284-286.
(Continued)

*Primary Examiner* — Edgardo San Martin
(74) *Attorney, Agent, or Firm* — Akerman LLP; Peter A. Chiabotti

(57) ABSTRACT

Earpieces and methods of forming earpieces for radio frequency (RF) mitigation are provided. An earpiece is configured to be inserted in an ear canal. The earpiece includes an insertion element and a sealing section disposed on the insertion element and configured to conform to the ear canal. The sealing section is configured to substantially mitigate radio frequency (RF) transmission and to substantially isolate the ear canal from an ambient environment.

17 Claims, 4 Drawing Sheets

Related U.S. Application Data continuation of application No. 13/486,514, filed on Jun. 1, 2012, now Pat. No. 10,362,381.

(60) Provisional application No. 61/492,193, filed on Jun. 1, 2011.

(51) Int. Cl.
| | |
|---|---|
| *A61F 2/18* | (2006.01) |
| *H05K 9/00* | (2006.01) |
| *H04R 1/02* | (2006.01) |
| *H04R 1/08* | (2006.01) |

(52) U.S. Cl.
CPC ............ *H04R 1/1091* (2013.01); *H04R 31/00* (2013.01); *H05K 9/00* (2013.01); *H05K 9/009* (2013.01); *H04R 1/023* (2013.01); *H04R 1/086* (2013.01); *Y10T 29/49005* (2015.01); *Y10T 29/4957* (2015.01)

(56) References Cited

U.S. PATENT DOCUMENTS

| | | | |
|---|---|---|---|
| 4,088,849 A | 5/1978 | Usami et al. | |
| 4,420,657 A | 12/1983 | Larkin | |
| 4,830,139 A | 5/1989 | Cirillo | |
| 4,947,440 A | 8/1990 | Bateman et al. | |
| 5,208,867 A | 5/1993 | Stites, III | |
| 5,267,321 A | 11/1993 | Langberg | |
| 5,524,056 A | 6/1996 | Killion et al. | |
| 5,564,085 A * | 10/1996 | Chen ................ | H01Q 1/245 455/117 |
| 5,654,530 A | 8/1997 | Sauer et al. | |
| 5,903,868 A | 5/1999 | Yuen et al. | |
| 5,996,584 A | 12/1999 | Oliveira et al. | |
| 6,021,207 A | 2/2000 | Puthuff et al. | |
| 6,021,325 A | 2/2000 | Hall | |
| 6,163,338 A | 12/2000 | Johnson et al. | |
| 6,163,508 A | 12/2000 | Kim et al. | |
| 6,226,389 B1 | 5/2001 | Lemelson et al. | |
| 6,298,323 B1 | 10/2001 | Kaemmerer | |
| 6,359,993 B2 | 3/2002 | Brimhall | |
| 6,367,578 B1 | 4/2002 | Shoemaker | |
| 6,400,652 B1 | 6/2002 | Goldberg et al. | |
| 6,411,722 B1 * | 6/2002 | Wolf ................ | H04R 1/1058 381/370 |
| 6,415,034 B1 | 7/2002 | Hietanen | |
| 6,473,512 B1 | 10/2002 | Juneau et al. | |
| 6,567,524 B1 | 5/2003 | Svean et al. | |
| RE38,351 E | 12/2003 | Iseberg et al. | |
| 6,661,901 B1 | 12/2003 | Svean et al. | |
| 6,724,902 B1 | 4/2004 | Shennib et al. | |
| 6,728,385 B2 | 4/2004 | Kvaloy et al. | |
| 6,748,238 B1 | 6/2004 | Lau | |
| 6,754,359 B1 | 6/2004 | Svean et al. | |
| 6,804,638 B2 | 10/2004 | Fiedler | |
| 6,804,643 B1 | 10/2004 | Kiss | |
| 7,072,482 B2 | 7/2006 | Van Doorn et al. | |
| 7,107,109 B1 | 9/2006 | Nathan et al. | |
| 7,164,775 B2 | 1/2007 | Meyer et al. | |
| 7,209,569 B2 | 4/2007 | Boesen | |
| 7,424,123 B2 | 9/2008 | Shennib et al. | |
| 7,430,299 B2 | 9/2008 | Armstrong et al. | |
| 7,433,714 B2 | 10/2008 | Howard et al. | |
| 7,450,730 B2 | 11/2008 | Bertg et al. | |
| 7,477,756 B2 | 1/2009 | Wickstrom et al. | |
| 7,480,387 B2 | 1/2009 | Meyer et al. | |
| 7,562,020 B2 | 6/2009 | Le et al. | |
| 7,580,537 B2 | 8/2009 | Urso et al. | |
| 7,756,281 B2 | 7/2010 | Goldstein et al. | |
| 7,756,285 B2 | 7/2010 | Sjursen et al. | |
| 7,778,434 B2 | 8/2010 | Juneau et al. | |
| 7,920,557 B2 | 4/2011 | Moote | |
| 8,014,553 B2 | 9/2011 | Radivojevic et al. | |
| 8,047,207 B2 | 11/2011 | Perez et al. | |
| 8,194,864 B2 | 6/2012 | Goldstein et al. | |
| 8,199,919 B2 | 6/2012 | Goldstein et al. | |
| 8,208,644 B2 | 6/2012 | Goldstein et al. | |
| 8,208,652 B2 | 6/2012 | Keady | |
| 8,221,861 B2 | 7/2012 | Keady | |
| 8,229,128 B2 | 7/2012 | Keady | |
| 8,251,925 B2 | 8/2012 | Keady et al. | |
| 8,312,960 B2 | 11/2012 | Keady | |
| 8,437,492 B2 | 5/2013 | Goldstein et al. | |
| 8,493,204 B2 | 7/2013 | Wong et al. | |
| 8,522,916 B2 | 9/2013 | Keady | |
| 8,550,206 B2 | 10/2013 | Keady et al. | |
| 8,554,350 B2 | 10/2013 | Keady et al. | |
| 8,600,067 B2 | 12/2013 | Usher et al. | |
| 8,631,801 B2 | 1/2014 | Keady | |
| 8,657,064 B2 | 2/2014 | Staab et al. | |
| 8,678,011 B2 | 3/2014 | Goldstein et al. | |
| 8,718,313 B2 | 5/2014 | Keady | |
| 8,750,295 B2 | 6/2014 | Liron | |
| 8,848,939 B2 | 9/2014 | Keady et al. | |
| 8,917,880 B2 | 12/2014 | Goldstein et al. | |
| 8,992,710 B2 | 3/2015 | Keady | |
| 9,037,458 B2 | 5/2015 | Park et al. | |
| 9,113,267 B2 | 8/2015 | Usher et al. | |
| 9,123,323 B2 | 9/2015 | Keady | |
| 9,123,343 B2 | 9/2015 | Kurki-Suonio | |
| 9,135,797 B2 | 9/2015 | Couper et al. | |
| 9,138,353 B2 | 9/2015 | Keady | |
| 9,185,481 B2 | 11/2015 | Goldstein et al. | |
| 9,216,237 B2 | 12/2015 | Keady | |
| 9,539,147 B2 | 1/2017 | Keady et al. | |
| 9,757,069 B2 | 9/2017 | Keady et al. | |
| 9,781,530 B2 | 10/2017 | Usher et al. | |
| 9,843,854 B2 | 12/2017 | Keady | |
| 10,012,529 B2 | 7/2018 | Goldstein et al. | |
| 10,190,904 B2 | 1/2019 | Goldstein et al. | |
| 10,362,381 B2 * | 7/2019 | Goldstein ............ | H04R 1/1016 |
| 10,418,016 B2 * | 9/2019 | Goldstein ............... | A61F 11/10 |
| 10,575,081 B2 * | 2/2020 | Goldstein ............ | H04R 1/1091 |
| 2001/0046304 A1 | 11/2001 | Rast | |
| 2002/0106091 A1 | 8/2002 | Furst et al. | |
| 2002/0118798 A1 | 8/2002 | Langhart et al. | |
| 2003/0040345 A1 | 2/2003 | Berger | |
| 2003/0123686 A1 | 7/2003 | Berger | |
| 2003/0161097 A1 | 8/2003 | Le et al. | |
| 2003/0165246 A1 | 9/2003 | Kvaloy et al. | |
| 2004/0042103 A1 | 3/2004 | Mayer | |
| 2004/0109668 A1 | 6/2004 | Stuckman | |
| 2004/0125965 A1 | 7/2004 | Alberth, Jr. et al. | |
| 2004/0190737 A1 | 9/2004 | Kuhnel et al. | |
| 2004/0196992 A1 | 10/2004 | Ryan | |
| 2004/0196996 A1 | 10/2004 | Feitel | |
| 2004/0203351 A1 | 10/2004 | Shearer et al. | |
| 2005/0078838 A1 | 4/2005 | Simon | |
| 2005/0123146 A1 | 6/2005 | Voix et al. | |
| 2005/0288057 A1 | 12/2005 | Lai et al. | |
| 2006/0067551 A1 | 3/2006 | Cartwright et al. | |
| 2006/0083395 A1 | 4/2006 | Allen et al. | |
| 2006/0092043 A1 | 5/2006 | Lagassey | |
| 2006/0195322 A1 | 8/2006 | Broussard et al. | |
| 2006/0204014 A1 | 9/2006 | Isenberg et al. | |
| 2007/0043563 A1 | 2/2007 | Comerford et al. | |
| 2007/0086600 A1 | 4/2007 | Boesen | |
| 2007/0189544 A1 | 8/2007 | Rosenberg | |
| 2007/0291953 A1 | 12/2007 | Ngia et al. | |
| 2008/0031475 A1 | 2/2008 | Goldstein | |
| 2008/0037801 A1 | 2/2008 | Alves et al. | |
| 2008/0165988 A1 | 7/2008 | Terlizzi et al. | |
| 2009/0010456 A1 | 1/2009 | Goldstein et al. | |
| 2009/0022353 A1 | 1/2009 | Goldstein et al. | |
| 2009/0024234 A1 | 1/2009 | Archibald | |
| 2009/0071487 A1 | 3/2009 | Keady | |
| 2010/0012420 A1 * | 1/2010 | Keady .................... | A61F 11/08 181/135 |
| 2010/0061564 A1 | 3/2010 | Clemow et al. | |
| 2010/0166239 A1 | 7/2010 | Bilderback | |
| 2010/0177918 A1 | 7/2010 | Keady et al. | |
| 2010/0241256 A1 | 9/2010 | Goldstein et al. | |
| 2010/0296668 A1 | 11/2010 | Lee et al. | |

(56) References Cited

U.S. PATENT DOCUMENTS

| | | |
|---|---|---|
| 2011/0096939 A1 | 4/2011 | Ichimura |
| 2011/0235843 A1 | 9/2011 | Keady et al. |
| 2011/0264447 A1 | 10/2011 | Visser et al. |
| 2011/0293103 A1 | 12/2011 | Park et al. |
| 2013/0098706 A1 | 4/2013 | Keady |
| 2013/0149192 A1 | 6/2013 | Keady |
| 2014/0003644 A1 | 1/2014 | Keady et al. |
| 2014/0026665 A1 | 1/2014 | Keady |
| 2014/0373854 A1 | 12/2014 | Keady |
| 2016/0015568 A1 | 1/2016 | Keady |
| 2016/0104452 A1 | 4/2016 | Guan et al. |
| 2016/0192077 A1 | 6/2016 | Keady |
| 2016/0295311 A1 | 10/2016 | Keady et al. |
| 2017/0134865 A1 | 5/2017 | Goldstein et al. |
| 2018/0054668 A1 | 2/2018 | Keady |
| 2018/0132048 A1 | 5/2018 | Usher et al. |
| 2018/0220239 A1 | 8/2018 | Keady et al. |
| 2019/0082272 A9 | 3/2019 | Goldstein et al. |

OTHER PUBLICATIONS

Bernard Widrow, John R. Glover Jr., John M. McCool, John Kaunitz, Charles S. Williams, Robert H. Hearn, James R. Zeidler, Eugene Dong Jr, and Robert C. Goodlin, Adaptive Noise Cancelling: Principles and Applications, Proceedings of the IEEE, vol. 63, No. 12, Dec. 1975.

Mauro Dentino, John M. McCool, and Bernard Widrow, Adaptive Filtering in the Frequency Domain, Proceedings of the IEEE, vol. 66, No. 12, Dec. 1978.

\* cited by examiner

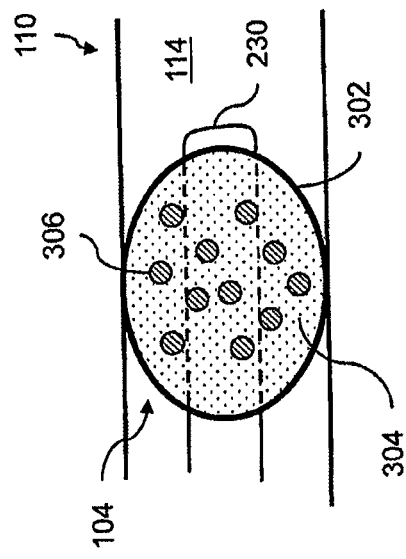
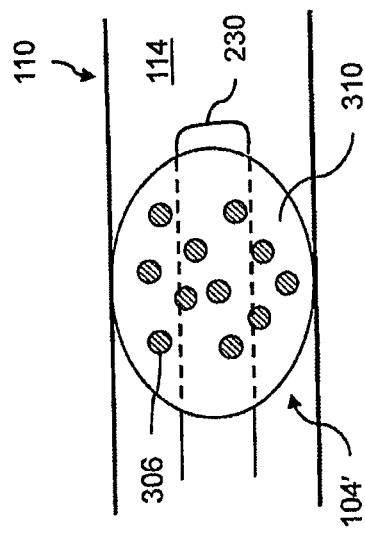
FIG. 3A
FIG. 3B

METHODS AND DEVICES FOR RADIO FREQUENCY (RF) MITIGATION PROXIMATE THE EAR

CROSS REFERENCE TO RELATED APPLICATIONS

This application is a continuation of U.S. application Ser. No. 13/735,175, filed 7 Jan. 2013, which is a continuation of U.S. application Ser. No. 13/486,514, filed Jun. 1, 2012 entitled METHODS AND DEVICES FOR RADIO FREQUENCY (RF) MITIGATION PROXIMATE THE EAR and claims the benefit of U.S. Provisional Application No. 61/492,193 entitled "METHODS AND DEVICES FOR RADIO FREQUENCY (RF) MITIGATION PROXIMATE THE EAR" filed on Jun. 1, 2011, the contents of which are incorporated herein by reference.

FIELD OF INVENTION

The present invention relates to earpieces and, more particularly, to earpieces and methods of forming earpieces for radio frequency (RF) mitigation proximate the ear.

BACKGROUND OF THE INVENTION

During data transmission, communication devices (such as mobile phones) may emit radio frequency (RF) waves, a form of electromagnetic radiation. There are generally two types of electromagnetic radiation, ionizing and non-ionizing radiation. It is known that large doses of ionizing radiation (for example, X-rays, ultraviolet (UV) rays, and gamma rays) may cause cancer. There is concern that non-ionizing radiation (for example, visible light, microwaves and RF waves) may also cause cancer. Recent studies have indicated that there may be a link between the non-ionizing radiation (such as the radiation emitted from mobile phones) and cancer.

SUMMARY OF THE INVENTION

The present invention relates to an earpiece configured to be inserted in an ear canal. The earpiece includes an insertion element and a sealing section disposed on the insertion element and configured to conform to the ear canal. The sealing section is configured to substantially mitigate RF transmission and to substantially isolate the ear canal from an ambient environment.

The present invention also relates to an earpiece configured to be inserted in an ear canal of an ear. The earpiece includes a stent, a housing coupled to the stent and a sealing section disposed on the stent and configured to conform to the ear canal. The sealing section is configured to substantially mitigate RF transmission from a communication device proximate the ear and to substantially isolate the ear canal from an ambient environment.

The present invention also relates to methods of forming an earpiece. The method includes forming an insertion element, forming a sealing section to substantially mitigate RF transmission and attaching the sealing section to the insertion element. The sealing section is configured to conform to an ear canal and to substantially isolate the ear canal from an ambient environment.

BRIEF DESCRIPTION OF THE DRAWINGS

The invention may be understood from the following detailed description when read in connection with the accompanying drawing. It is emphasized, according to common practice, that various features of the drawing may not be drawn to scale. On the contrary, the dimensions of the various features may be arbitrarily expanded or reduced for clarity. Moreover, in the drawing, common numerical references are used to represent like features. Included in the drawing are the following figures:

FIGS. 3A and 3B are cross-section diagrams of exemplary sealing sections, according to embodiments of the present invention.

DETAILED DESCRIPTION OF THE INVENTION

Aspects of the present invention relate to earpieces and methods of forming earpieces for RF mitigation proximate the ear. An exemplary earpiece may include an insertion element and a sealing section disposed on the insertion element. The sealing section is configured to be inserted in an ear canal and may be configured to conform to the ear canal. According to an exemplary embodiment, the sealing section may be configured to substantially absorb RF radiation. According to another embodiment, the insertion element may also be configured to substantially absorb RF radiation. Accordingly, the earpiece may absorb RF emission and provide sound isolation from an ambient environment. According to an exemplary embodiment, the sealing section may include an expandable element filled with a medium and particles configured to absorb the RF emission. According to another exemplary embodiment, the sealing section may include a sealing material and particles configured to absorb the RF emission.

According to an exemplary embodiment, an exemplary earpiece may include at least one transducer. A transducer may be configured to receive a sound signal from a communication device coupled to the earpiece and to transmit the sound signal to the ear canal. The communication device may emit RF radiation. Accordingly, exemplary earpieces of the present invention may be coupled to one or more communication devices and may provide acoustic signals to the ear canal, while providing RF mitigation to the ear canal from RF radiation emitted by the communication device.

Figure 1:
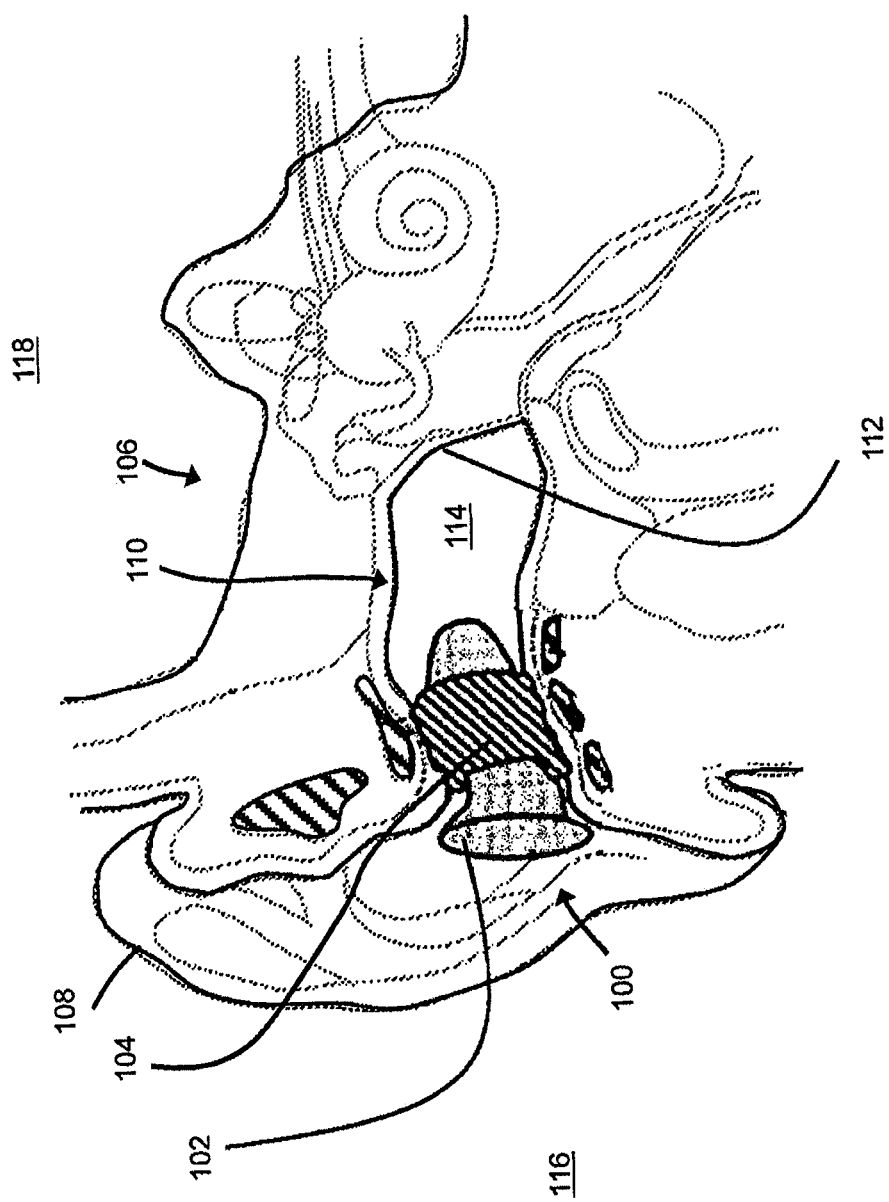
FIG. 1 is a side-view diagram of an exemplary earpiece inserted in an ear, according to an embodiment of the present invention.

Referring to FIG. 1, a side-view diagram of an exemplary earpiece 100 is shown. Earpiece 100 is shown relative to ear 106 of user 118. FIG. 1 also illustrates a general physiology of ear 106. An external portion of ear 106 includes pinna 108. An internal portion of ear 106 includes ear canal 110 and tympanic membrane 112 (i.e., an eardrum).

Pinna 108 is a cartilaginous region of ear 106 that focuses acoustic information from ambient environment 116 to ear canal 110. In general, sound enters ear canal 110 and is subsequently received by tympanic membrane 112. Acoustic information resident in ear canal 110 vibrates tympanic membrane 112. The vibration is converted to a signal (corresponding to the acoustic information) that is provided to an auditory nerve (not shown).

Earpiece 100 may include insertion element 102 operatively coupled to sealing section 104. Earpiece 100 may be configured to be inserted into ear canal 110, such that sealing section 104 forms sealed volume 114 (also referred to herein as sealed cavity 114) between sealing section 104 and tympanic membrane 112. Sealing section 104 may be configured to seal ear canal 110 from sound (i.e., provide sound isolation from ambient environment 116 external to ear canal 110).

Figure 2:
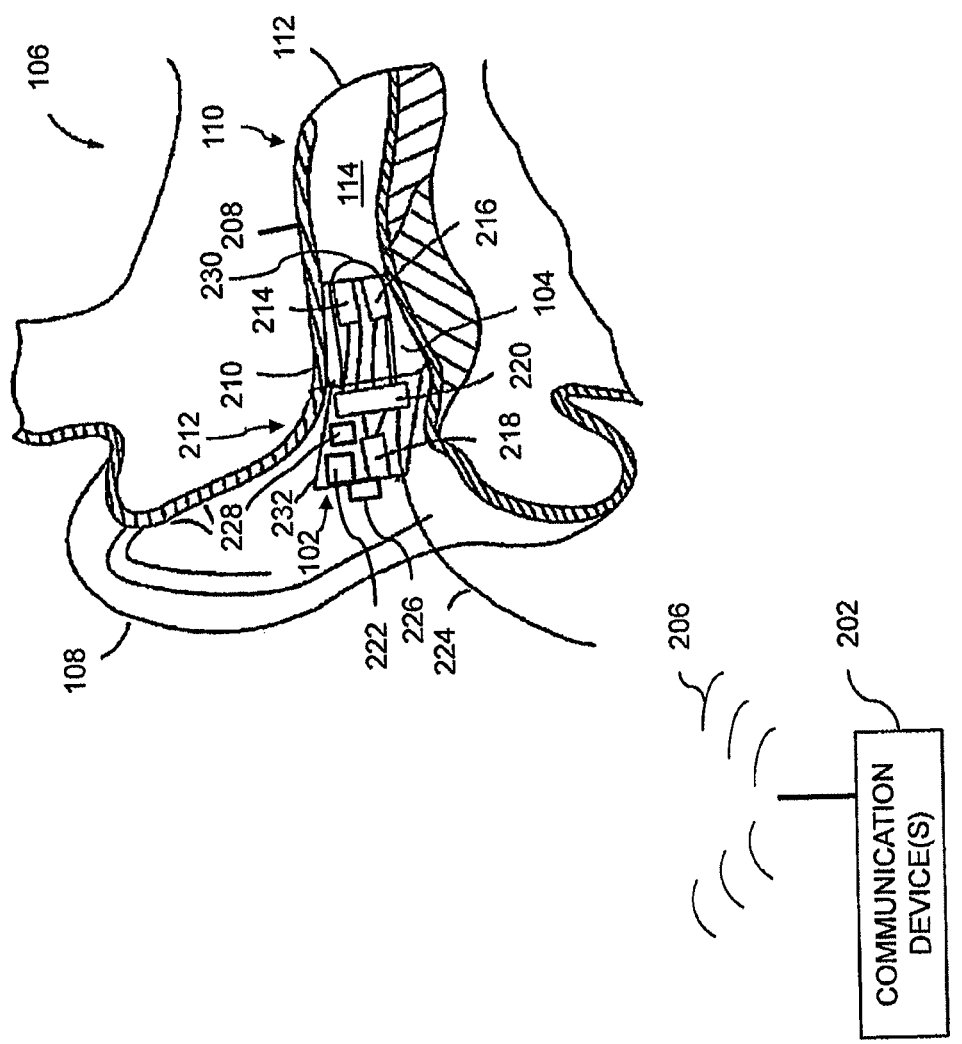
FIG. 2 is a cross-section diagram of the earpiece shown in FIG. 1 which may receive RF radiation, illustrating one or more components that may be included in the earpiece, according to an exemplary embodiment of the present invention.

As described further below, sealing section 104 may be configured to substantially absorb RF radiation 206 (FIG. 2) (i.e., RF transmission) emitted from communication device 202 (FIG. 2). Insertion element 102 may also be configured to substantially absorb RF emission.

Referring next to FIG. 2, a cross-section diagram of earpiece 100 in ear 106 is shown. FIG. 2 illustrates one or more components which may be included in earpiece 100. In general, earpiece 100 may be configured to be inserted into ear canal 110, and to form an acoustic seal (via sealing section 104) with walls 208 of ear canal 110 at a location 210 between entrance 212 to ear canal 110 and tympanic membrane 112.

FIG. 2 also illustrates communication device 202 proximate to ear 106. Although one communication device 202 is shown, it is understood that there may more than one communication device 202 which may be proximate to ear 106. In general, communication device 202 may emit (i.e., transmit) RF radiation 206 which may reach ear 106. Communication device 202 may include, for example, a mobile phone or a digital wireless system such as a data communication network. In general, communication device 202 may include any device that may emit RF radiation 206.

Sealing section 104 is described further below with respect to FIGS. 3A and 36. In general, sealing section 104 may be configured to interfere with, absorb and/or reflect RF radiation 206 (i.e., to provide RF mitigation of RF radiation 206).

Insertion element 102 may be formed from, for example, thermoplastic elastomer (TPE) materials, materials having an elastomeric property (such as silicone), or other malleable materials capable of conforming to the ear canal. According to an exemplary embodiment, insertion element 102 may also be configured to provide mitigation of RF radiation 206. For example, insertion element 102 may be impregnated with an RF damping material such as a TPE filled with graphite and/or nickel powder. In general, RF mitigation components in earpiece 100 (in sealing section 104 and/or in insertion element 102) may be electrically coupled and/or grounded to user 118 or an alternate acceptable location.

Insertion element 102 may include stent 230 and housing 232. Stent 230 and/or housing 232 may include one or more components of earpiece 100, described further below. Sealing section 104 may be disposed on stent 230, such that stent 230 is also inserted in ear canal 110. Housing 232 may be coupled to stent 230 and may be placed at entrance 212 to ear canal 110. According to an exemplary embodiment, at least one of stent 230 or housing 232 may be configured to provide mitigation of RF radiation 206. In FIG. 2, earpiece 100 is illustrated as being disposed in ear 106. It is understood that various components of earpiece 100 may also be configured to be placed behind ear 106 or may be placed partially behind ear 100 and partially in ear 100.

According to an exemplary embodiment, earpiece 100 may be configured to communicate with communication device 202. According to another embodiment, earpiece 100 may be configured as a sound isolation device (described further below) and thus, may not be configured to communicate with communication device 202.

As shown in FIG. 2, insertion element 102 may include one or more components, such as electro-acoustical components, electrical components and/or pumping mechanism 228 for sealing section 104. Several example embodiments of components that may be included in insertion element 102 are discussed below.

According to one embodiment, earpiece 100 may include insertion element 102 and sealing section 104, without any electro-acoustic elements. In this embodiment, earpiece 100 may be configured simply as a sound isolation device, where sealing section 104 and/or insertion element 102 are configured to substantially mitigate RF radiation 206 from communication device 202. In this manner, RF radiation 206 may be substantially mitigated and/or prevented from reaching closed cavity 114 of ear canal 110. If sealing section 104 is configured to be expanded (such as described with respect to FIG. 3A), housing 232 may include pumping mechanism 228 to provide medium 304 (FIG. 3A) to sealing section 104 via stent 230.

According to another embodiment, earpiece 100 may include one or more electro-acoustical components (i.e., transducers). For example, stent 230 may include ear canal receiver (ECR) 214 (i.e., a loudspeaker). ECR 214 may be configured to provide acoustic content to sealed volume 114. ECR 214 may receive the acoustic content from communication device 202 or any other device capable of providing acoustic content (such as a portable audio player).

As a result of the seal provided by sealing section 104, ECR 214 may be able to generate a full range bass response time when reproducing sounds for user 118 (FIG. 1). The seal (by sealing section 104) may also significantly reduce a sound pressure level at tympanic membrane 112 resulting from the sound field at entrance 212 to ear canal 110 (to provide sound isolation).

According to another exemplary embodiment, stent 230 may include ear canal microphone (ECM) 216 located adjacent to ECR 214, which may also be acoustically coupled to sealed cavity 114. ECM 216 may measure a sound pressure level in sealed cavity 114. For example, the sound pressure level in sealed cavity 114 may be measured as a part of testing a hearing acuity of user 118 (FIG. 1). The sound pressure level in sealed cavity 114 may also be used to confirm an integrity of the acoustic seal of sealing section 104, as well as the working conditions of ECM 216 and ECR 214.

According to another exemplary embodiment, housing 232 may include ambient sound microphone (ASM 218). ASM 218 may monitor a sound pressure at entrance 212 to (occluded) ear canal 110. The sound pressure monitored by ASM 218 may be used, for example, to adjust the sound isolation provided by sealing section 104. As another example, the sound pressure monitored by ASM 218 may be used to adjust a volume of the audio content provided by ECR 214 to closed cavity 114.

All transducers (such as ECR 214, ECM 216 and ASM 218) may respectively receive or transmit audio signals to control circuit 220 in housing 232. Control circuit 220 may undertake at least a portion of the audio signal processing described above. Control circuit 220 may include, for example, a logic circuit, a digital signal processor or a microprocessor. Although not shown, earpiece 100 may also include a memory to store one or more signals from ECR 214, ECM 216 and ASM 218. As another example, earpiece 100 may be coupled to a memory that is remote from earpiece 100. The memory may include, for example, a random access memory (RAM), a magnetic disk, an optical disk, flash memory or a hard drive. Although ECR 214 and ECM 216 are shown in FIG. 2 as being in stent 230, it is understood that one or more of ECR 214 and ECM 216 may be formed in housing 232 and coupled to closed cavity 114 via acoustic channels formed in stent 230.

Housing 232 may also include communication circuit 222 coupled to control circuit 220. In general, communication circuit 222 may be configured to receive and/or transmit signals to earpiece 100. Communication circuit 222 may be configured to communicate with communication device 202 via communication path 224. Communication path 224 may include a wired or wireless connection. It is understood that any transceivers (not shown) of communication circuit 222 may be positioned on housing 232 such that they are out of range of the RF mitigation provided by sealing section 104 and/or insertion element 102, such that the RF mitigation provided by earpiece 100 may not interfere with data transmission and/or reception by communication circuit 222.

According to another exemplary embodiment, housing 232 may include user interface 226. Housing 232 may also include pumping mechanism 228 for controlling expansion of sealing section 104. User interface 226 may be configured to control one or more of ECR 214, ECM 216, ASM 218, control circuit 220, communication circuit 222 and pumping mechanism 228. ECR 214, ECM 216, ASM 218, control circuit 220, communication circuit 222, user interface 226 and pumping mechanism 228 may be coupled together via a data and control bus (not shown). It is understood that earpiece 100 may include additional components (not shown) such as a battery.

Referring next to FIGS. 3A and 3B, exemplary sealing sections 104, 104' are shown. In particular, FIG. 3A is a cross-section diagram of sealing section 104 including expandable element 302 (such as a balloon) filled with medium 304; and FIG. 3B is a cross-section diagram of sealing section 104' in ear canal 110 including sealing material 310. Each of sealing section 104 and sealing section 104' may include particles 306 to substantially absorb RF radiation 206 (FIG. 2) (for example, between about 3 kHz to about 300 GHz).

Referring to FIG. 3A, sealing section 104 may include expandable element 302 filled with medium 304 mixed with particles 306 (for example, suspended in solution). Sealing section 104 is configured to substantially attenuate sound from ambient environment 116 (FIG. 1). Sealing section 104 is also configured to substantially absorb RF radiation 206 (FIG. 2) via particles 306. In general, particles 306 may be configured to interfere with, absorb and/or reflect RF radiation 206 (FIG. 2).

Expandable element 302 may include balloons of various shapes, sizes and materials, for example constant volume balloons (low elasticity<=50% elongation under pressure or stress) and variable volume (high elastic>50% elongation under pressure or stress) balloons. Pumping mechanism 228 (FIG. 2) may be used to provide medium 304 to expandable element 302.

Expandable element 302 may be formed from any compliant material that has a low permeability to medium 304. Examples of materials of expandable element 302 include any suitable elastomeric material, such as, without being limited to, silicone, rubber (including synthetic rubber) and polyurethane elastomers (such as Pellethane® and Santoprene™). Materials of expandable element 302 may be used in combination with a barrier layer (for example, a barrier film such as SARANEX™), to reduce the permeability of expandable element 302. In general, expandable element 302 may be formed from any suitable material having a range of Shore A hardness between about 5 A and about 90 A, with an elongation of about 500% or greater. Expandable element 302 may also be made of RF absorbing elastomers such as a polyurethane filled with electrically conductive material such as iron graphite and/or nickel particles.

Medium 304 may include, without being limited to, electrically conductive liquids such as saline and colloidal liquids that have carrier fluids including, for example, fluorocarbon liquids such as Flourinert™ (manufactured by 3M™) (including, for example, FC-770), ethylene glycol and isopropyl alcohol (with particles 306 suspended in solution).

Medium 304 may include any suitable liquid or gel capable of expanding and contracting expandable element 302 and that would maintain a comfortable level of pressure for user 118 (FIG. 1) of earpiece 100. In general, examples of medium 304 include, without being limited to, silicone, non or low permeable-based polymers, gels, fluorocarbon liquids, ethylene glycol, isopropyl alcohol or saline.

Particles 306 may include ferromagnetic particles, ferrimagnetic particles or electrically conductive particles such as graphite, nickel, and/or iron. As understood by one of skill in the art, particles 306 may be formed large enough to provide adequate radio frequency interference (RFI) shielding and may be formed small enough to not impede a mechanical operation of earpiece 100 (FIG. 1). In an exemplary embodiment, a size of particles 306 may range from about 0.11 Jm to about 1001 Jm in diameter. In general, particles 306 may include any suitable particles configured to interfere with, absorb and/or reflect RF radiation 206 (FIG. 2). Although particles 306 are described herein, it is understood that medium may include fibers instead of or in addition to particles 306. The fibers may also be formed of ferromagnetic material, ferrimagnetic material or electrically conductive material, as described above with respect to particles 306.

As shown in FIG. 3B, sealing section 104' is similar to sealing section 104 (FIG. 3A), except that sealing section 104' includes sealing material 310 having embedded particles 306 for substantially mitigating RF radiation 206 (FIG. 2). Thus, sealing section 104' may also be configured to seal ear canal 110 from ambient sound 116 (FIG. 1).

Sealing material 310 may include, without being limited to, foam, rubber or any suitable sealing material capable of conforming to ear canal 110 and for sealing ear canal 110 to provide sound isolation. Sealing material 310 may also be composed of RF damping materials such as a polyurethane and or any other applicable polymer or rubber such as silicone filled with RF shielding materials such as nickel, graphite, and/or iron particles.

In general, earpiece 100 (FIG. 1) may provide RF shielding by using any suitable electrically conductive material. Because metals are typically not flexible and may be difficult form into a suitable earpiece shape (such as by injection molding), in an exemplary embodiment, conductive particles/fibers may be used as fillers to make polymers conductive (and thus to provide effective RF shielding materials).

According to another exemplary embodiment, at least one of insertion element 102 or sealing section 104 may be formed from a flexible material that is inherently conductive, without using fillers (such as conductive particles and/or fibers). For example, a metal earpiece body may be formed. An example of this is provided with respect to the medium 304 (FIG. 3A) used to fill expandable element 302.

If a fluid is conductive, it may be capable of provide RF shielding without fillers such as particles and/or fibers. However, based on the desired shielding characteristics (i.e., a frequency range of RF radiation and a desired reflectivity), fillers may be added to improve conductivity and thus, RF shielding. For example, the higher the conductivity and the thicker the material, the greater the shielding capability by the material, and the greater the shielding at lower frequencies. As is the case with solids, shielding ability may be afforded to nonconductive fluids by using conductive fillers.

Referring back to FIG. 2, although earpiece 100 is described above as being configured to mitigate RF radiation 206 from communication device 202, earpiece 100 may also be configured to mitigate RF radiation produced by earpiece 100 itself. For example, insertion element 102 and/or sealing section 104 may mitigate RF radiation emitted by communication circuit 222. In an exemplary embodiment, earpiece 100 may be configured to absorb between about 70% and about 100% of generated and/or received RF radiation within a frequency range of communication device 202 and internally generated radiation typically in a range between about 3 kHz and 300 GHz.

Figure 4:
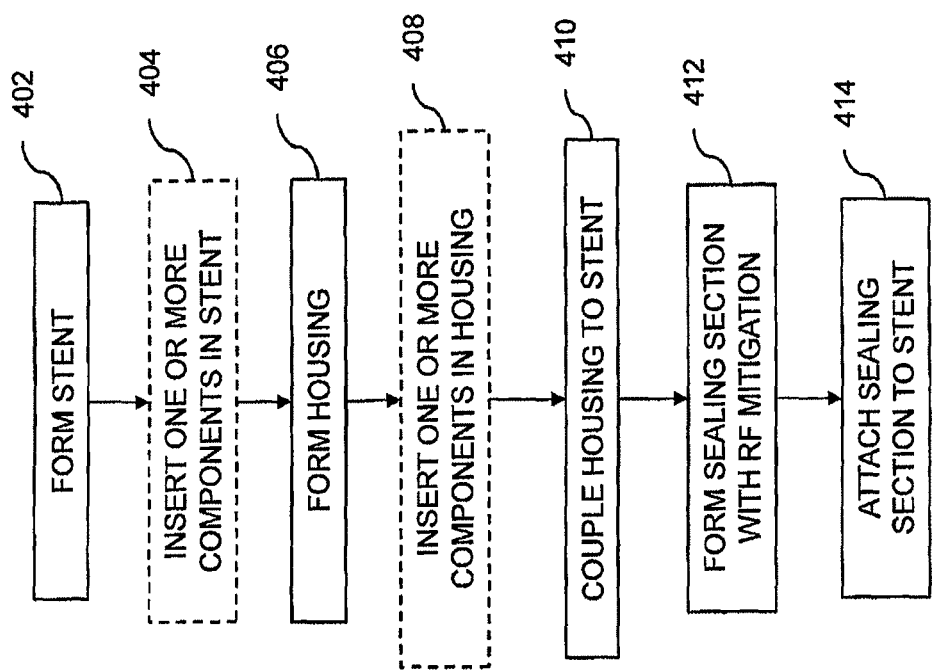
FIG. 4 is a flowchart diagram of an exemplary method of forming an earpiece for RF mitigation proximate the ear, according to an embodiment of the present invention.

Referring next to FIG. 4, a flowchart diagram of an exemplary method for forming an earpiece capable of RF mitigation is shown. The steps illustrated in FIG. 4 represent an example embodiment of the present invention. It is understand that certain steps may be performed in an order different from what is shown. It is also understood that certain steps may be eliminated.

At step 402, stent 230 (FIG. 2) is formed, for example, via injection molding. According to an exemplary embodiment, stent 230 (FIG. 2) may be formed with a material capable of RF mitigation. For example, stent 230 (FIG. 2) may be formed of an RF damping material such as polyurethane filled with RF shielding material such as iron, nickel and/or graphite particles. As another example, stent 230 (FIG. 2) may be formed of a material with embedded ferromagnetic particles, ferrimagnetic or electrically conductive particles for RF mitigation.

At optional step 404, one or more components may be inserted in stent 230 (FIG. 2). For example, as shown in FIG. 2, one or more electro-acoustic components (such as ECR 214 and/or ECM 216) may be formed in stent 230.

At step 406, housing 232 (FIG. 2) may be formed, for example, via injection molding. According to an exemplary embodiment, housing 232 (FIG. 2) may be formed with a material capable of RF mitigation. For example, housing 232 (FIG. 2) may be formed of an RF damping material such as polyurethane filled with RF shielding material such as iron, nickel, and/or graphite particles. As another example, housing 232 (FIG. 2) may be formed of a material with embedded ferromagnetic particles, ferrimagnetic or electrically conductive particles for RF mitigation.

At optional step 408, one or more components may be inserted in housing 232 (FIG. 2). For example, as shown in FIG. 2, electro-acoustic components (such as ASM 218), electrical components (such as control circuit 220, communication circuit 222 and/or user interface 226) and/or other components (such as pumping mechanism 228) may be formed in housing 232. At step 410, housing 232 (FIG. 2) is coupled to stent 230.

At step 412, sealing section 104 (FIG. 1) is formed such that it includes RF mitigation properties. For example, sealing section 104 may include medium 304 (FIG. 3A) and particles 306 for RF mitigation or may include sealing material 310 (FIG. 3B) with embedded particles 306 for RF mitigation. Sealing material 310 (FIG. 3B) may also be formed of RF damping material such as polyurethane filled with RF shielding materials such as iron, nickel and/or graphite particles.

At step 414, sealing section 104 (FIG. 2) is attached to stent 230. Sealing section 104 (FIG. 2) may be attached to stent 230 via any suitable attachment method, such as, but not limited to, bonding, adherence with an adhesive, thermal bonding, molding and ultrasonic bonding.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A earphone comprising:
an Ambient Sound Microphone (ASM), where the ASM is part of the earphone, where the ASM generates a first ASM signal;
a loudspeaker, where the loudspeaker is configured to play audio;
a pump; and
a sealing section, where the sealing section is configured to reduce radio frequency (RF) transmission past the sealing section when compared to a sealing section composed of silicone, where the sealing section is configured to attenuate acoustical waves at 1000 Hz by more than 5 dB, wherein the sealing section further includes:
an expandable element; and
a filler medium which includes a fluid and particles wherein the pump is configured to move the fluid and particles in and out of the expandable element.

2. The earphone according to claim 1, where the expandable element is attached to a stent and where the expandable element includes: a deformable membrane encompassing a volume.

3. The earphone according to claim 1, where the particles absorb more than 50% of the incident RF radiation on the particles at a target RF frequency.

4. The earphone according to claim 1, where the particles reflects more than 50% of the incident RF radiation on the particles at a target RF frequency.

5. The earphone according to claim 3, where the target RF frequencies lies between 3 kHz and 300 GHz.

6. The earphone according to claim 4, where the target RF frequencies lies between 3 kHz and 300 GHz.

7. The earphone according to claim 5, where the membrane forms a constant volume balloon.

8. The earphone according to claim 6, where the membrane forms a constant volume balloon.

9. The earphone according to claim 5, where the membrane forms a variable volume balloon.

10. The earphone according to claim 6, where the membrane forms a variable volume balloon.

11. The earphone according to claim 5, where the membrane is composed of at least one of silicone, rubber, and polyurethane elastomers.

12. The earphone according to claim 6, where the membrane is composed of at least one of silicone, rubber, and polyurethane elastomers.

13. The earphone according to claim 5, where the membrane is composed of an RF absorbing elastomer.

14. The earphone according to claim 6, where the membrane is composed of an RF reflecting elastomer.

15. The earphone according to claim 1, where the expandable element is formed of a material having a Shore A value between 5 A and 90 A.

16. The earphone according to claim 2, where the fluid medium is a silicone fluid, permeable-based polymer, gel, fluorocarbon liquids, ethylene glycol, isopropyl alcohol or a saline solution.

17. The earphone according to claim 1, where the particles include at least one of ferromagnetic particles, ferrimagnetic particles, or electrically conductive particles.

\* \* \* \* \*